United States Patent
Hlavinka et al.

(10) Patent No.: US 8,940,228 B2
(45) Date of Patent: Jan. 27, 2015

(54) SLIDABLE CLAMP FOR PORT ISOLATION

(71) Applicant: Terumo BCT Biotechnologies, LLC, Lakewood, CO (US)

(72) Inventors: Dennis J. Hlavinka, Arvada, CO (US); David Bihm, Denver, CO (US); Keith Manica, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 91 days.

(21) Appl. No.: 13/738,881

(22) Filed: Jan. 10, 2013

(65) Prior Publication Data

US 2013/0177476 A1 Jul. 11, 2013

Related U.S. Application Data

(60) Provisional application No. 61/585,482, filed on Jan. 11, 2012.

(51) Int. Cl.
*A61L 2/00* (2006.01)
*B01J 19/08* (2006.01)
(Continued)

(52) U.S. Cl.
CPC .... *F16L 3/12* (2013.01); *A61J 1/10* (2013.01); *A61J 1/1412* (2013.01);
(Continued)

(58) Field of Classification Search
CPC ............. A61L 2/00; A61L 9/00; A61L 9/18; A61L 9/20; A61L 9/205
USPC ................ 422/1, 22–24, 28, 186.04; 604/250
See application file for complete search history.

(56) References Cited

U.S. PATENT DOCUMENTS

| | | |
|---|---|---|
| 485,698 A | 11/1892 | Ketchum |
| 823,068 A | 6/1906 | Mosley |

(Continued)

FOREIGN PATENT DOCUMENTS

| | | |
|---|---|---|
| EP | 0206997 B1 | 6/1986 |
| EP | 0799627 A2 | 10/1997 |

(Continued)

OTHER PUBLICATIONS

International Search Report and Written Opinion, PCT/US2006/042934, Mar. 6, 2007.

(Continued)

*Primary Examiner* — Monzer R Chorbaji
(74) *Attorney, Agent, or Firm* — Elizabeth J. Reagan; René A. Pereyra; John R. Merkling

(57) ABSTRACT

Embodiments described herein generally relate to an apparatus and methods for preventing the recontamination of a pathogen-reduced fluid by pathogens trapped in one or more ports of an inactivation fluid container. Through the use of a slidable clamp positioned in an area of the container immediately adjacent to a port to be isolated, the port may be sealed to prevent any liquid product from entering the port and associated tubing when liquid product is added to the container. The slidable clamp includes a slot, in which the distal end of the slot has a larger width than the proximal end of the slot. The width of the slot at the narrowest, most proximal portion allows for a fluid-tight seal to be created when the slidable clamp is slid into the closed position with respect to the port to be isolated.

27 Claims, 7 Drawing Sheets

(51) Int. Cl.
- *A61M 5/00* (2006.01)
- *F16L 3/12* (2006.01)
- *A61J 1/10* (2006.01)
- *A61J 1/14* (2006.01)
- *A61M 39/28* (2006.01)

(52) U.S. Cl.
CPC .......... *A61M 39/287* (2013.01); *A61M 39/286* (2013.01); *A61J 1/1475* (2013.01); *A61L 2/0076* (2013.01); *A61L 2202/22* (2013.01)
USPC .......... 422/22; 422/24; 422/186.04; 604/250

(56) References Cited

U.S. PATENT DOCUMENTS

| | | |
|---|---|---|
| 3,247,852 A | 4/1966 | Schneider |
| 3,316,935 A | 5/1967 | Kaiser et al. |
| 3,698,681 A | 10/1972 | Lacey |
| 3,822,052 A | 7/1974 | Lange |
| 3,900,184 A | 8/1975 | Burke et al. |
| 3,942,228 A | 3/1976 | Buckman et al. |
| 4,053,135 A | 10/1977 | Saliaris |
| 4,091,815 A | 5/1978 | Larsen |
| 4,112,944 A | 9/1978 | Williams |
| 4,193,174 A | 3/1980 | Stephens |
| 4,235,412 A | 11/1980 | Rath et al. |
| 4,248,401 A | 2/1981 | Mittleman |
| 4,428,745 A | 1/1984 | Williams |
| 4,434,963 A | 3/1984 | Russell |
| 4,439,179 A | 3/1984 | Lueders et al. |
| 4,453,295 A | 6/1984 | Laszczower |
| 4,469,227 A | 9/1984 | Faust |
| 4,588,160 A | 5/1986 | Flynn et al. |
| 4,589,626 A | 5/1986 | Kurtz et al. |
| 4,643,389 A | 2/1987 | Elson et al. |
| 4,673,161 A | 6/1987 | Flynn et al. |
| 4,726,949 A | 2/1988 | Miripol et al. |
| 4,787,406 A | 11/1988 | Edwards et al. |
| 4,807,622 A | 2/1989 | Ohkaka et al. |
| 4,830,510 A | 5/1989 | Bellhouse |
| 4,866,282 A | 9/1989 | Miripol et al. |
| 4,878,896 A | 11/1989 | Garrison et al. |
| 4,952,812 A | 8/1990 | Miripol et al. |
| 5,026,019 A | 6/1991 | Biekart et al. |
| 5,035,399 A | 7/1991 | Rantanen-Lee |
| D325,631 S | 4/1992 | Daoud et al. |
| 5,203,056 A | 4/1993 | Funk et al. |
| 5,207,642 A | 5/1993 | Orkin et al. |
| 5,238,218 A | 8/1993 | Mackal |
| 5,401,256 A * | 3/1995 | Stone et al. .................. 604/250 |
| 5,423,769 A | 6/1995 | Jonkman et al. |
| 5,429,615 A | 7/1995 | Starchevich |
| 5,464,388 A | 11/1995 | Merte et al. |
| 5,496,301 A | 3/1996 | Hlavinka et al. |
| 5,547,108 A | 8/1996 | Gsell et al. |
| 5,685,875 A | 11/1997 | Hlavinka et al. |
| 5,817,116 A | 10/1998 | Takahashi et al. |
| 5,853,398 A | 12/1998 | Lal et al. |
| 5,866,074 A | 2/1999 | Chapman et al. |
| 5,910,135 A | 6/1999 | Hadzic et al. |
| 5,941,842 A | 8/1999 | Steele et al. |
| 5,965,349 A | 10/1999 | Lin et al. |
| D427,307 S | 6/2000 | Guala et al. |
| 6,083,205 A | 7/2000 | Bourne et al. |
| 6,089,527 A | 7/2000 | Utterberg |
| 6,113,062 A | 9/2000 | Schnell et al. |
| D431,650 S | 10/2000 | Guala et al. |
| 6,129,330 A | 10/2000 | Guala |
| 6,158,319 A | 12/2000 | D'Silva |
| 6,161,812 A | 12/2000 | Guala et al. |
| 6,196,519 B1 | 3/2001 | Utterberg |
| 6,234,448 B1 | 5/2001 | Porat |
| 6,245,570 B1 | 6/2001 | Grimm et al. |
| 6,258,577 B1 | 7/2001 | Goodrich, Jr. et al. |
| 6,277,337 B1 | 8/2001 | Goodrich, Jr. et al. |
| 6,369,394 B1 | 4/2002 | Lee |
| D465,843 S | 11/2002 | Guala |
| 6,548,241 B1 | 4/2003 | McBurney et al. |
| 6,554,806 B2 | 4/2003 | Butterfield |
| 6,565,802 B1 | 5/2003 | Hanley et al. |
| 6,592,558 B2 | 7/2003 | Quah |
| 6,644,618 B1 | 11/2003 | Balbo |
| 6,648,017 B2 | 11/2003 | Lamas et al. |
| 6,696,023 B2 | 2/2004 | Grimm et al. |
| 6,740,239 B2 | 5/2004 | Hogberg et al. |
| 6,742,760 B2 | 6/2004 | Blickhan et al. |
| 6,843,961 B2 | 1/2005 | Hlavinka et al. |
| 6,869,653 B2 | 3/2005 | Ling et al. |
| 6,902,539 B2 | 6/2005 | Bainbridge et al. |
| 7,094,378 B1 | 8/2006 | Goodrich, Jr. et al. |
| 7,234,677 B2 | 6/2007 | Zerfas |
| 7,686,279 B2 | 3/2010 | Nerbonne et al. |
| 7,774,072 B2 | 8/2010 | Gerber |
| 7,780,644 B2 | 8/2010 | Miyajima et al. |
| 7,815,613 B2 | 10/2010 | Raulerson et al. |
| 8,048,055 B2 | 11/2011 | Hlavinka et al. |
| 8,403,291 B2 | 3/2013 | Howlett et al. |
| 2002/0043051 A1 | 4/2002 | Manica et al. |
| 2002/0138066 A1* | 9/2002 | Manica et al. ................ 604/410 |
| 2004/0186412 A1 | 9/2004 | Mallett et al. |
| 2008/0087126 A1 | 4/2008 | Oda et al. |

FOREIGN PATENT DOCUMENTS

| | | |
|---|---|---|
| EP | 0610778 B1 | 5/2000 |
| EP | 1000633 A2 | 5/2000 |
| EP | 1389473 A1 | 2/2004 |
| EP | 0995461 B1 | 9/2004 |
| EP | 0995462 B1 | 9/2004 |
| JP | 05146484 | 6/1993 |
| WO | 98/13093 A1 | 4/1998 |
| WO | 98/22164 A1 | 5/1998 |
| WO | 03/082181 A2 | 10/2003 |
| WO | 03/086479 A1 | 10/2003 |
| WO | 20041047714 A1 | 6/2004 |
| WO | 20061049842 A1 | 5/2006 |
| WO | 20101141564 A2 | 12/2010 |

OTHER PUBLICATIONS

International Search Report and Written Opinion, PCT/US2006/062291, Nov. 26, 2007.

International Search Report and Written Opinion, PCT/US2013/021082, May 2, 2013.

* cited by examiner

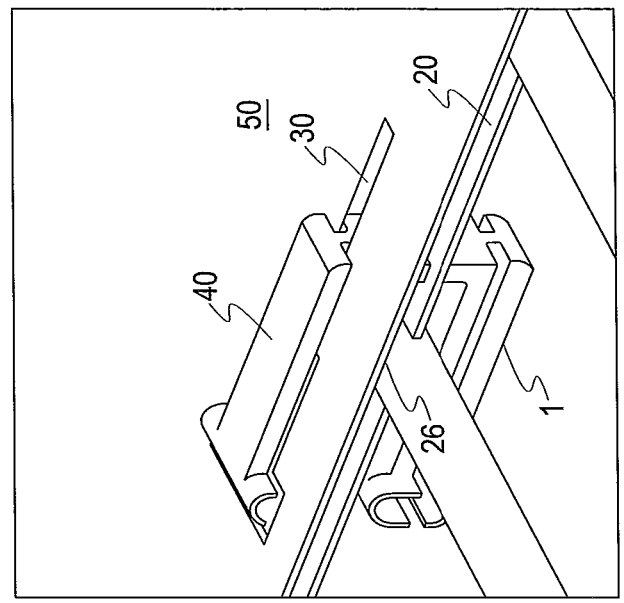
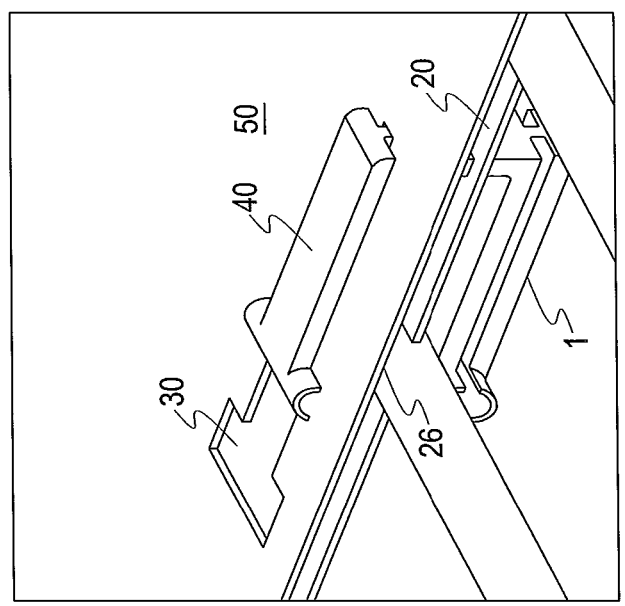

SLIDABLE CLAMP FOR PORT ISOLATION

CROSS-REFERENCE TO RELATED APPLICATION

This application claims priority to U.S. Provisional Patent Application Ser. No. 61/585,482, filed on Jan. 11, 2012 and entitled, "SLIDABLE CLAMP FOR PORT ISOLATION," which is hereby incorporated by reference in its entirety as if set forth herein in full.

BACKGROUND

The contamination of human blood and blood components with pathogens such as human immunodeficiency virus (HIV), hepatitis and bacteria creates a serious risk for patients who receive blood or blood components via blood transfusions. Whole blood, packed red blood cells, platelets, and plasma (either fresh or fresh frozen) are examples of transfusable blood and blood components which may be contaminated with pathogens. To help combat this problem, blood, blood components, and other fluids can be decontaminated using photosensitizers which, when activated by exposure to light, inactivate pathogens which may be contained in the fluid without destroying the biological activity of the fluid.

A fluid container commonly used as a pathogen reduction container may contain a number of ports which provide ingress and egress into and out of the container. In order to provide selective communication between the interior of the container and exterior of the container, a frangible connection mechanism or other type of connector capable of being opened is commonly used in a port. Numerous frangible mechanisms are known in the art. Rupturing a frangible mechanism in a port allows a portion of the mechanism to be separated from the remaining portions of the mechanism, thereby permitting fluid to flow through the port. With such separation, the separated portion of the frangible mechanism is left to float in the fluid contained in the interior of the container or bag, which may be undesirable. Furthermore, when the separated portion of the frangible mechanism is separated from the rest of the mechanism, debris and particulates can possibly break off from the frangible mechanism during the breaking process. Such debris and particulates may therefore also be left to float in the fluid contained in the bag. Eliminating the use of a frangible mechanism in a port of a bag could thus eliminate the separated portion of the frangible mechanism altogether and minimize the presence of any resulting debris in the fluid contained in the bag.

Further, where ports provide ingress and egress into and out of a fluid container, a portion of the fluid to be inactivated during a pathogen inactivation procedure may become trapped or remain within one or more of the ports, such that the photosensitizer is not able to be adequately distributed or mixed with the trapped fluid. Without adequate interaction of the photosensitizer with the trapped fluid, pathogen inactivation of the fluid caught in the ports may be hampered or prevented altogether. Additionally, the ports may be substantially opaque, which may prevent the passage of photoradiation to the fluid contained within the ports. As a result, fluid trapped within the ports may still contain pathogenic contaminants after the inactivation process is completed, and such contaminants may then redistribute within the otherwise inactivated fluid, reinfecting the fluid.

It is to both the prevention of recontamination of the pathogen reduced fluid by pathogens trapped in the ports of an inactivation container and to the elimination of a frangible mechanism and the like to seal off a port that the present disclosure is directed.

SUMMARY

Embodiments of the present disclosure generally relate to providing an apparatus and methods for preventing the recontamination of a pathogen reduced fluid by pathogens trapped in one or more ports of an inactivation container. Aspects of particular embodiments provide for the use of a slidable clamp coupled to a fluid container. In an embodiment, the coupling of the clamp to the fluid container comprises positioning the clamp in an opening, slit, recess, or indentation, for example, of the container. Where a slit, for example, in the fluid container is used, the slit is positioned immediately adjacent to a port, such as an outlet port, to be isolated. By sliding the clamp in the slit such that a slot in the clamp compresses the port to close the port, the port may be sealed to prevent any liquid from entering the port when such liquid fills the container. Closing the port thus isolates the port from any fluid entering the container. After the fluid in the container is pathogen reduced or inactivated, the outlet port may be opened without risking contamination to the exiting fluid as the fluid is transferred out of the container through the outlet port.

The disclosure relates to a method for using a clamp to isolate a port of a fluid container. The method includes the steps of closing, with the clamp, a first outlet port of the fluid container, in which the closing comprises coupling the clamp to the fluid container adjacent to the first outlet port. The closing further comprises sliding the clamp to position the first outlet port in a slot of the clamp, in which the slot comprises a first portion at a distal end of the slot and a second portion at a proximal end of the slot, the first portion of the slot comprising a first width and the second portion of the slot comprising a second width. In an embodiment, the first width is larger than the second width. The closing further comprises moving the clamp, from the first portion of the slot to the second portion of the slot, over the first outlet port to close the first outlet port. The method further includes the steps of adding a fluid to the fluid container after the closing of the first outlet port of the fluid container, in which the fluid comprises a liquid product to be pathogen inactivated; adding a photosensitizer to the fluid container; illuminating the fluid container; and inactivating a pathogen in the fluid container to produce an inactivated fluid.

In at least one embodiment, the method further comprises opening, with the clamp, the first outlet port, after inactivating the pathogen in the fluid container to produce the inactivated fluid. The method also includes transferring the inactivated fluid out of the fluid container.

In at least one embodiment, the closing, with the clamp, the first outlet port of the fluid container comprises isolating the first outlet port of the fluid container to prevent the liquid product from entering the first outlet port.

In at least one embodiment, the first outlet port is closed when it occupies a proximal end of the second portion of the slot.

In at least one embodiment, the moving of the clamp further comprises the slot moving over the first outlet port at the distal end of the slot; and the slot compressing the first outlet port, in which the compressing comprises the slot moving over the first outlet port at the proximal end of the slot such that the first outlet port occupies a proximal end of the second portion of the slot.

In at least one embodiment, the clamp comprises a first alignment indicator on an upper portion of the clamp, in which the first alignment indicator on the upper portion of the clamp aligns with a second alignment indicator on the fluid container to indicate that the clamp is in a closed position.

In at least one embodiment, the clamp comprises a first alignment indicator on a lower portion of the clamp, in which the first alignment indicator on the lower portion of the clamp aligns with a second alignment indicator on the fluid container to indicate that the clamp is in a closed position.

In at least one embodiment, the method further comprises removing a kit organizer from the fluid container after the closing, with the clamp, the first outlet port of the fluid container.

In at least one embodiment, the kit organizer causes the first outlet port to be open during sterilization of the fluid container.

In at least one embodiment, the coupling the clamp to the fluid container comprises positioning the clamp in a first slit in the fluid container.

In at least one embodiment, a kit organizer comprises a second slit corresponding to the first slit in the fluid container.

In at least one embodiment, the coupling the clamp to the fluid container comprises positioning the clamp in a recess in the fluid container.

In at least one embodiment, the coupling the clamp to the fluid container comprises positioning the clamp in an indentation in the fluid container.

The disclosure further relates to a port isolation apparatus, in which the apparatus comprises a fluid container including a first coupling structure in a weld area of the fluid container. The fluid container comprises a first outlet port, in which the first outlet port is adjacent to the first coupling structure in the weld area of the fluid container. The apparatus also comprises a clamp connected to the first coupling structure of the fluid container, in which the clamp comprises a slot, the slot comprising a first portion at a distal end of the slot and a second portion at a proximal end of the slot, the first portion of the slot comprising a first width and the second portion of the slot comprising a second width. In an embodiment, the first width is larger than the second width. In an embodiment, the first outlet port is positioned in the slot of the clamp as the clamp is slid over the first outlet port to close a lumen of the first outlet port.

In at least one embodiment, the clamp comprises a first alignment indicator on an upper portion of the clamp, in which the first alignment indicator on the upper portion of the clamp aligns with a second alignment indicator on the fluid container to indicate that the clamp is in a closed position.

In at least one embodiment, the first outlet port of the fluid container is closed when the first outlet port occupies the second portion of the slot.

In at least one embodiment, the fluid container further comprises a second outlet port, in which the second outlet port is adjacent to a second coupling structure in the weld area of the fluid container.

In at least one embodiment, the slot communicates with the first coupling structure such that the slot traverses the first coupling structure along the slot. The first outlet port enters the slot at the distal end of the slot, in which the first outlet port is compressed as the first outlet port moves to the proximal end of the slot.

In at least one embodiment, the first coupling structure in the weld area of the fluid container is a slit.

In at least one embodiment, the first coupling structure in the weld area of the fluid container is a recess.

In at least one embodiment, the first coupling structure in the weld area of the fluid container is an indentation.

The disclosure further relates to a clamp to isolate a port of a fluid container, the clamp comprising an upper portion comprising an upper portion front surface substantially similar to an upper portion back surface; a back portion connected at substantially ninety degrees to the upper portion; a lower portion connected at substantially ninety degrees to the back portion, in which the lower portion and the upper portion are substantially parallel to each other, the lower portion comprising a lower portion front surface substantially similar to a lower portion back surface. The clamp further comprises a slot separating the upper portion and the lower portion, in which the slot comprises a first portion at a distal end of the slot and a second portion at a proximal end of the slot, the first portion of the slot comprising a first width and the second portion of the slot comprising a second width. In an embodiment, the first width is larger than the second width. The clamp further comprises a first groove extending longitudinally along the lower portion front surface and the lower portion back surface to a distal end of the clamp.

In at least one embodiment, the clamp further comprises a first alignment indicator located on the clamp.

In at least one embodiment, the clamp further comprises a second alignment indicator located on a lower surface of the lower portion of the clamp. In an embodiment, the first alignment indicator is located on an upper surface of the upper portion of the clamp.

In at least one embodiment, the first alignment indicator on the upper portion of the clamp is configured to align with a third alignment indicator on the fluid container to indicate that the clamp is in a closed position.

In at least one embodiment, the second width of the second portion of the slot is substantially uniform from a distal end of the second portion of the slot to a proximal end of the second portion of the slot.

In at least one embodiment, the clamp further comprises a second groove extending longitudinally along the upper portion front surface and the upper portion back surface to the distal end of the clamp.

In at least one embodiment, the first groove and the second groove are configured to align the clamp with a kit organizer.

This Summary is included to provide a selection of concepts in a simplified form, in which such concepts are further described below in the Detailed Description. This Summary is not intended to be used in any way to limit the claimed subject matter's scope. Features, including equivalents and variations thereof, may be included in addition to those provided herein.

BRIEF DESCRIPTION OF THE DRAWINGS

Embodiments of the present disclosure may be described by referencing the accompanying figures. In the figures, like numerals refer to like items.

FIG. 10A illustrates a perspective view of a kit organizer and slidable clamp positioned through an opening or slit in a fluid container such that the outlet port is open in accordance with embodiments of the present disclosure.

FIG. 10B depicts a perspective view of a kit organizer and slidable clamp positioned through an opening or slit in a fluid container such that the outlet port is closed in accordance with embodiments of the present disclosure.

DETAILED DESCRIPTION

The following Detailed Description provides a discussion of illustrative embodiments with reference to the accompanying drawings. The inclusion of specific embodiments herein should not be construed as limiting or restricting the present disclosure. Further, while language specific to features, acts, and/or structures, for example, may be used in describing embodiments herein, the claims are not limited to the features, acts, and/or structures described. A person of skill in the art will appreciate that other embodiments, including improvements, are within the spirit and scope of the present disclosure.

Embodiments of the present disclosure are generally directed to a slidable clamp for creating a fluid-tight seal in a port of a fluid container, such as a blood bag. In an embodiment, one or more coupling structures, such as openings, slits, recesses, or indentations, for example, in an RF welded area of a fluid container are made immediately adjacent to the port(s) to be isolated. As used herein, the terms "couple," "coupled," "coupling," "coupling structure," and "coupling mechanism," for example, can refer to any mechanical connection or force communication between two or more parts or components. In embodiments, the slidable clamp is connected to a coupling structure, e.g., a first coupling structure, of the fluid container. For example, in an embodiment where openings or slits in the fluid container are used, the slidable clamp is operably associated with such slits by positioning and sliding the clamp into or through the slits to seal the desired port(s). In embodiments, the slit keeps the clamp in position during sterilizing and shipping. In another embodiment, a feature, such as a barb on the clamp leg, for example, is included on the clamp to assure that the clamp remains in position, such as open position, for example, until the user or customer is ready to use the fluid container or bag.

Prior to filling the bag with fluid or liquid product, the customer slides the clamp into the closed position to effectively close or isolate the desired port. Once an outlet port is closed, liquid product may then be added to the bag without having any such liquid enter the outlet port and associated tubing, according to embodiments.

In embodiments, it is possible that the entry portion of the outlet port may be exposed to liquid added to the fluid container. However, the entry portions of the container are readily exposed to light and are readily washed out during agitation of the product during illumination. Hence, recontamination from entry portion contact with the liquid to be pathogen inactivated should not occur.

Figure 1:
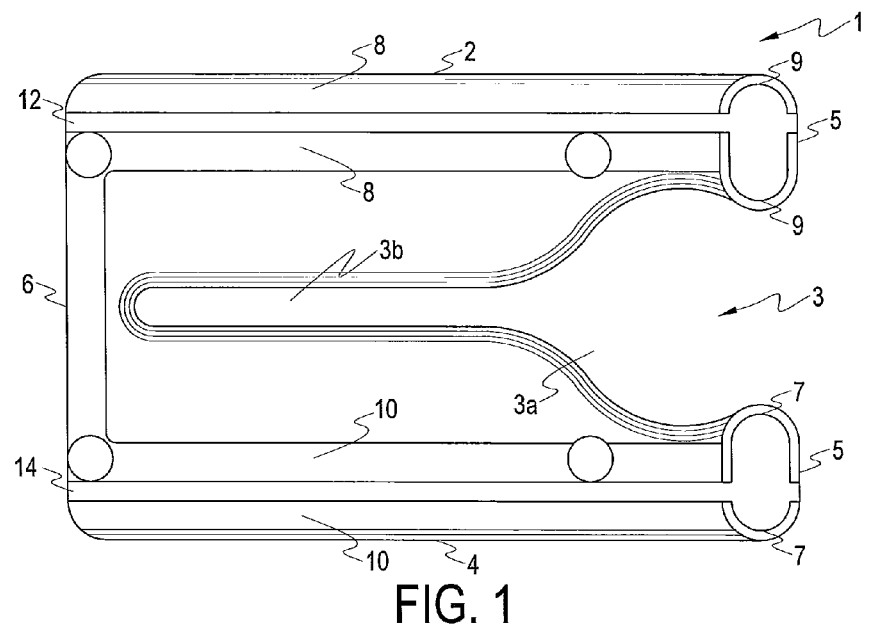
FIG. 1 illustrates a slidable clamp in accordance with embodiments of the present disclosure.
Figure 2:
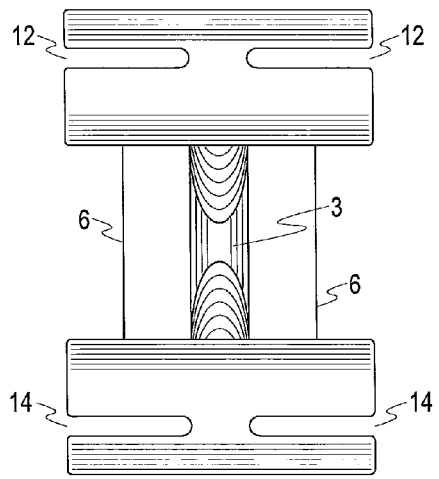
FIG. 2 depicts a front view, or from the distal end to the proximal end, of the slidable clamp of FIG. 1 in accordance with embodiments of the present disclosure.
Figure 3:
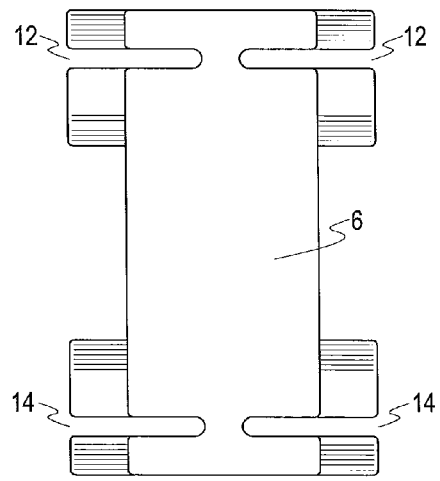
FIG. 3 illustrates a back view, or from the proximal end to the distal end, of the slidable clamp of FIG. 1 in accordance with embodiments of the present disclosure.

With reference to FIG. 1, a side view of slidable clamp 1 is shown. FIGS. 2 and 3 show alternate views of slidable clamp 1. FIG. 2 shows a front view, or from the distal end to the proximal end, of clamp 1, and FIG. 3 depicts a back view, or from the proximal end to the distal end, of clamp 1. Slidable clamp 1 generally includes an upper portion or leg 2 and a lower portion or leg 4, which are connected to each other by a back portion 6. The back portion 6 is connected at ninety degrees (90°) or substantially ninety degrees (90°) to the upper portion or leg 2. The back portion 6 is also connected at ninety degrees (90°) or substantially ninety degrees (90°) to the lower portion or leg 4. The upper portion 2 and lower portion 4 are parallel or substantially parallel to each other and form a slot 3 between the upper portion 2 and the lower portion 4. Upper portion 2 and lower portion 4 are thus separated from each other by slot 3. The upper portion 2 and the lower portion 4 have a proximal end at the back portion 6 and distal ends 5. In general, various features of clamp 1 may be referred to as each comprising a distal end and a proximal end. The distal end of features in general may be viewed as at or approaching distal ends 5, while the proximal end of features in general may be viewed as at or approaching back portion 6.

Slot 3 is formed in the distal ends 5 of the upper portion 2 and lower portion 4 and terminates before the back portion 6 such that slot 3 itself has a distal end 5 and a proximal end (terminating before back portion 6). In embodiments, the distal end 5 of slot 3 has a greater or larger diameter or width or opening of the slot 3 than the proximal end of slot 3. The proximal end of slot 3 thus has a smaller diameter or opening size or width of the slot 3 than the distal end of slot 3. The width of slot 3 narrows from the distal end 5 of slot 3 to the proximal end of slot 3. In an embodiment, the slot width is uniform or constant or substantially uniform or constant for at least a portion of the length of slot 3. For example, the slot width is uniform or constant or substantially uniform or constant as the proximal end of slot 3 is approached. According to embodiments, the portion of slot 3 (at or near the proximal end of slot 3) having a uniform or constant or substantially uniform or constant slot width is referred to as the second portion 3b of slot 3, while the portion of slot 3 having a changing width (at or near the distal end 5 of slot 3) is referred to as the first portion 3a of slot 3. The first portion 3a of slot 3 thus has a different or substantially different width or diameter or opening size from the distal end of the first portion 3a to the proximal end of the first portion 3a. On the other hand, the second portion 3b has the same or substantially the same slot width or diameter or opening size from the distal end of the second portion 3b to the proximal end of the second portion 3b. According to an embodiment, the first portion 3a of slot 3 has a first width, and the second portion 3b of slot 3 has a second width, in which the first width is greater or larger than the second width. In embodiments, an outlet port is closed when it occupies the second portion 3b of slot 3 such that the lumen of the port is compressed entirely to create a fluid-tight seal. Alternatively, the outlet port is open when it occupies the first portion 3a of slot 3.

In another embodiment, slot 3 extends longitudinally through clamp 1, increasing in the diameter or width of the opening of the slot from the proximal back portion 6 toward the distal ends 5 of the clamp. The diameter of the slot 3 at the narrowest, most proximal portion of slot 3 is such that when a port is slid into the slot, or, alternatively, when the slidable clamp 1 is slid over, or moves over, the port such that the port is positioned in the slot 3 of the clamp, the lumen of the port is compressed entirely, creating a fluid-tight seal.

In accordance with embodiments, upper portion 2 of clamp 1 has identical or similar, or substantially identical or similar, front 8 and back (not shown) surfaces. Lower portion 4 of clamp 1 also has identical or similar, or substantially identical or similar, front 10 and back (not shown) surfaces. In an embodiment, the lower portion front surface is thus substantially identical or similar to the lower portion back surface. Further, in an embodiment, the upper portion front surface is substantially identical or similar to the upper portion back surface. A groove 12 runs longitudinally along the entire length of the front 8 and back surface (not shown) of the upper portion 2, from the proximal back portion 6 to the distal end 5. A groove 14 also runs longitudinally along the entire length of the front 10 and back surface (not shown) of the lower portion 4 from the proximal back portion 6 to the distal end 5.

Figure 6:
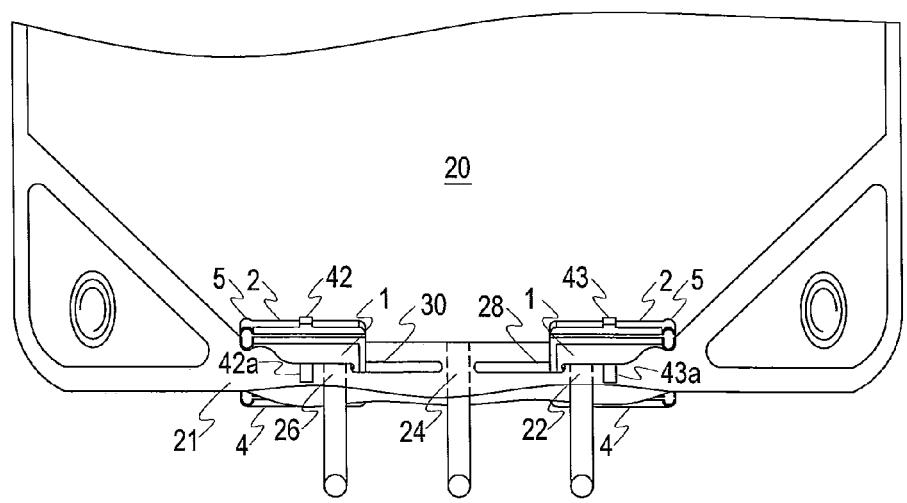
FIG. 6 depicts a perspective view of a portion of the fluid container shown in FIG. 4, in which such portion illustrates the outlet ports of the fluid container in closed positions, in accordance with embodiments of the present disclosure.
Figure 8:
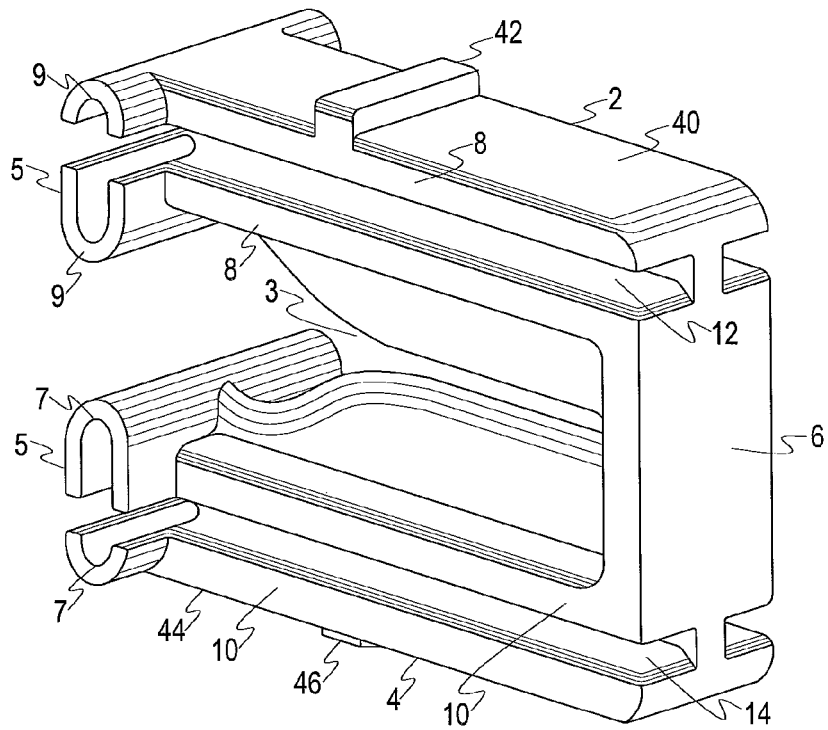
FIG. 8 depicts a perspective view of the slidable clamp illustrated in FIG. 1, including alignment indicators, in accordance with embodiments of the present disclosure.
Figure 9:
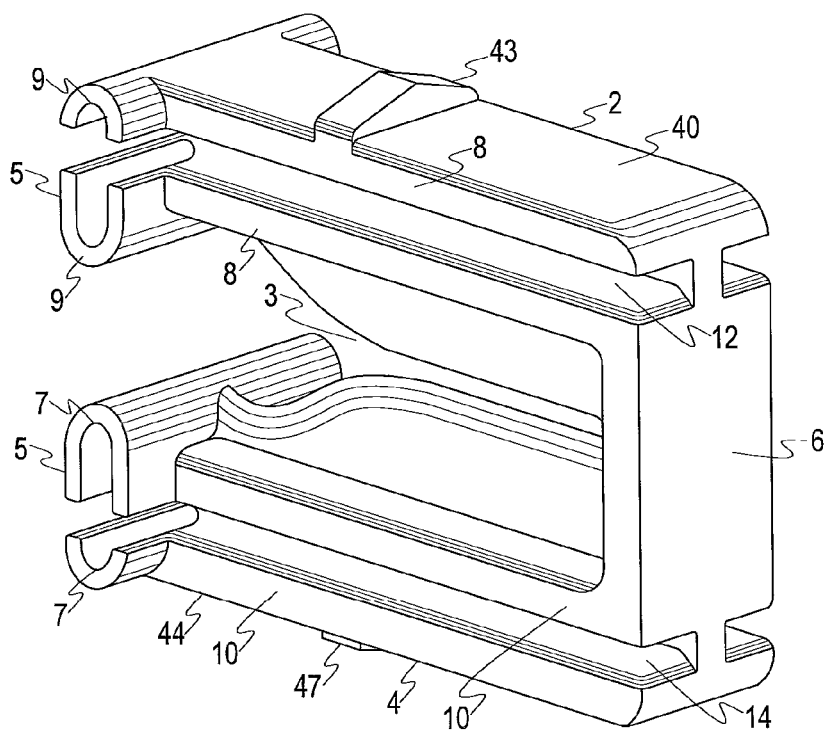
FIG. 9 depicts a perspective view of the slidable clamp illustrated in FIG. 1, including alignment indicators, in accordance with embodiments of the present disclosure.

As illustrated in FIGS. 8 and 9, for example, upper portion 2 of clamp 1 also has an upper surface 40. FIGS. 8 and 9 are multi-dimensional views of the slidable clamp 1 shown in FIG. 1, including the illustration of alignment indicators on the slidable clamp. According to an embodiment, an alignment indicator 42 is located on the upper surface 40 of upper portion 2 of the slidable clamp depicted in FIG. 8. In an alternative embodiment, an alignment indicator 43 is located on the upper surface 40 of upper portion 2 of the slidable clamp depicted in FIG. 9. Alignment indicators 42 and 43 have different shapes, as depicted in FIGS. 8 and 9. Many types, shapes, and orientations of alignment indicators may be used with the slidable clamp and fluid container without departing from the spirit and scope of the present disclosure. In an embodiment, the alignment indicators 42 and/or 43 line up, or align, with a corresponding alignment indicator(s) 42a or 43a (as shown in FIG. 6, for example) on the bag to let the user know when the clamp is in a closed position, and the port is fluidly closed. As indicated, the alignment indicators used with the slidable clamp and fluid container may be horizontal, vertical, etc. Many types, shapes, and orientations of alignment indicators may be used in accordance with embodiments of the present disclosure.

As shown in FIG. 8, lower portion 4 of clamp 1 also has a lower surface 44. According to an embodiment, an alignment indicator 46 is located on the lower surface 44 of lower portion 4. In a further embodiment, an alignment indicator 47 is located on the lower surface 44 of lower portion 4 of the slidable clamp depicted in FIG. 9. In an embodiment, the alignment indicator, such as alignment indicator(s) 46 or 47, for example, indicates closure of the port when the indicator is positioned over the top of the port. In yet another embodiment, the alignment indicators, such as 46 and/or 47, for example, line up, or align, with a corresponding alignment indicator(s) on the bag to indicate to the user that the clamp is in a closed position, and the port is fluidly closed. In a further embodiment, the alignment indicators, such as 46 and/or 47, for example, line up, or align, with multiple alignment indicators on the bag or container to indicate that the clamp is in a closed position. For example, in an embodiment, a first alignment indicator, such as 42a or 43a, for example (as shown in FIG. 6) on the bag 20 lines up with the alignment indicator 46 and/or 47, while a second and/or third alignment indicator(s) on the bag lines up with the distal and/or proximal ends of the clamp 1 when the clamp 1 is in a position that closes the port.

In an embodiment, alignment indicators, such as 46 and 47, for example, have different shapes. In yet another embodiment, alignment indicators, such as 46 and 47, for example, have the same, or substantially the same, shape. As noted, many types, shapes, and orientations of alignment indicators may be used with the slidable clamp and fluid container without departing from the spirit and scope of the present disclosure. For example, a first alignment indicator may be located on the upper surface of the upper portion of the clamp with a second alignment indicator located on a lower surface of the lower portion of the clamp. The first alignment indicator on the upper portion is configured to line up, or align, with a third alignment indicator on the fluid container to indicate that the clamp is in a closed position. Further, the second alignment indicator on the lower portion is configured to line up, or align itself, with a fourth indicator on the fluid container to indicate that the clamp is in a closed position. In another embodiment, the second alignment indicator on the lower portion is configured to line up, or align itself, with the third alignment indicator on the fluid container to indicate that the clamp is in a closed position. Thus, in accordance with embodiments, the container may include multiple alignment indicators, a single alignment indicator, or no additional alignment indicator, for example.

In embodiments, after the port to be isolated is closed, the container may then be filled with fluid, such as the fluid to be pathogen inactivated and a photosensitizer. In embodiments, the photosensitizer used is an endogenous photosensitizer. For example, endogenous photosensitizers include, but are not limited to, 7,8-dimethyl-10-ribityl isoalloxazine (riboflavin); 7,8,10-trimethylisoalloxazine; 7,8,-dimethylalloxazine; vitamin L; vitamin Ks; napththalenes; napththoquinones; and naphthols. These photosensitizers absorb to nucleic acids, in which their photodynamic effect may impact microorganisms and viruses in the fluid without affecting the biological activity, e.g., cells or proteins, of the fluid itself.

Figure 7:
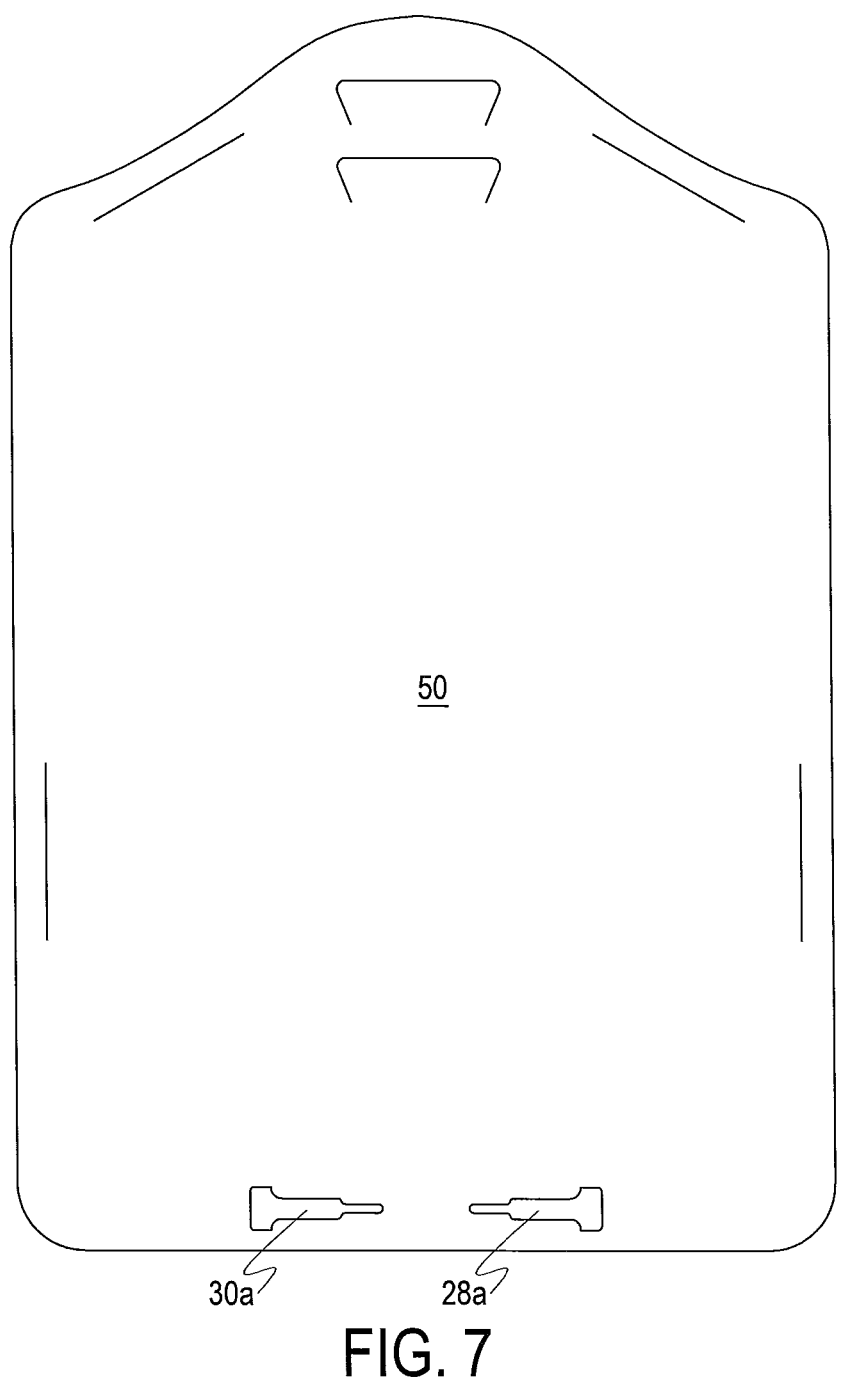
FIG. 7 illustrates a fluid container organizer in accordance with embodiments of the present disclosure.

The distal ends 5 of upper 2 and lower 4 portions of clamp 1 (shown in FIG. 1, for example) have outward facing edges or feet 9 and 7, respectively, protruding outwardly from the front surfaces 8 and 10, respectively, and back surfaces. In an embodiment, the feet 9 and 7 allow the user to slide the clamp 1 (with slot 3) within both the coupling structure, e.g., slit(s) 30 and/or 28, of the bag 20 (see FIG. 4, for example) and the corresponding coupling structure, e.g., slit(s) 30a and/or 28a, of a kit organizer 50 (shown in FIGS. 7, 10A, and 10B, for example), which may be used in embodiments. Turning to FIG. 7, for example, to ensure the slidable clamp 1 is kept open for sterilization and shipping, organizer 50 is used. Organizer 50 separates bag components during sterilizing and shipping and is designed to keep the slidable clamp 1 open during such processes. Organizer 50 is then removed by the user prior to use by placing the slidable clamp 1 in a closed position. For example, FIG. 10A depicts the kit organizer 50 attached to the fluid container 20. As shown, slidable clamp 1 is located in opening or slit 30 in the area of the bag 20 immediately adjacent to outlet port 26 (to be isolated). In an embodiment, opening or slit 30 may be in an RF welded area of the bag 20. Organizer 50 has a corresponding opening or slit to the opening or slit 30 in fluid container 20. As shown in FIG. 10A, slidable clamp 1 (shown with upper surface 40) is in the open position with respect to outlet port 26. In embodiments, organizer 50 cannot be removed while the slidable clamp 1 is in such open position. However, organizer 50 can be removed once the slidable clamp is placed in the closed position with respect to the outlet port, such as outlet port 26, as depicted in FIG. 10B.

According to an embodiment, the grooves 12 and 14 (as shown in FIGS. 1-3, for example) on the front and back surfaces of the clamp 1 are configured to help align the clamp 1 to organizer 50. Organizer 50 has a shape similar to that of bag 20 and is made of a semi-rigid material. Slot 3 of clamp 1 fits into a coupling structure, e.g., slits 28 or 30, of bag 20 and enables clamp 1 to slide back and forth along the slits 28 or 30 of the bag 20 and the corresponding coupling structure, e.g., slits 28a or 30a, in organizer 50. The grooves 12 and 14 fit in corresponding slits 28a and 30a in organizer 50 (as shown in FIG. 7, for example) to help keep clamp 1 in the open position. The open position of clamp 1 keeps the port(s) fluidly open. As noted, in embodiments, organizer 50 cannot be removed from the bag, such as bag 20, for example, unless the clamps 1 are in a closed position over the port(s). This feature ensures that the ports and associated tubing are kept open during sterilization and shipping.

According to embodiments, slidable clamp 1 may be made from any polymeric material which is suitable for medical applications and which is, preferably, resistant to failure upon undergoing illumination procedures and/or sterilization procedures common in the medical industry. Clamp 1 may be of unitary construction and injection molded as an integral device, according to an embodiment. In other embodiments, clamp 1 is constructed of multiple components connected together. Examples of materials suitable for construction of slidable clamp 1 include, but are not limited to, polycarbonate, polyolefin, and acetal resin (commercially known as DELRIN®). As illustrated in FIGS. 1-3, 8, and 9, for example, the surfaces of the slidable clamp 1 are, in embodiments, smooth and rounded in shape to avoid having any sharp surfaces which may puncture, or cause a hole in, bag 20.

Figure 4:
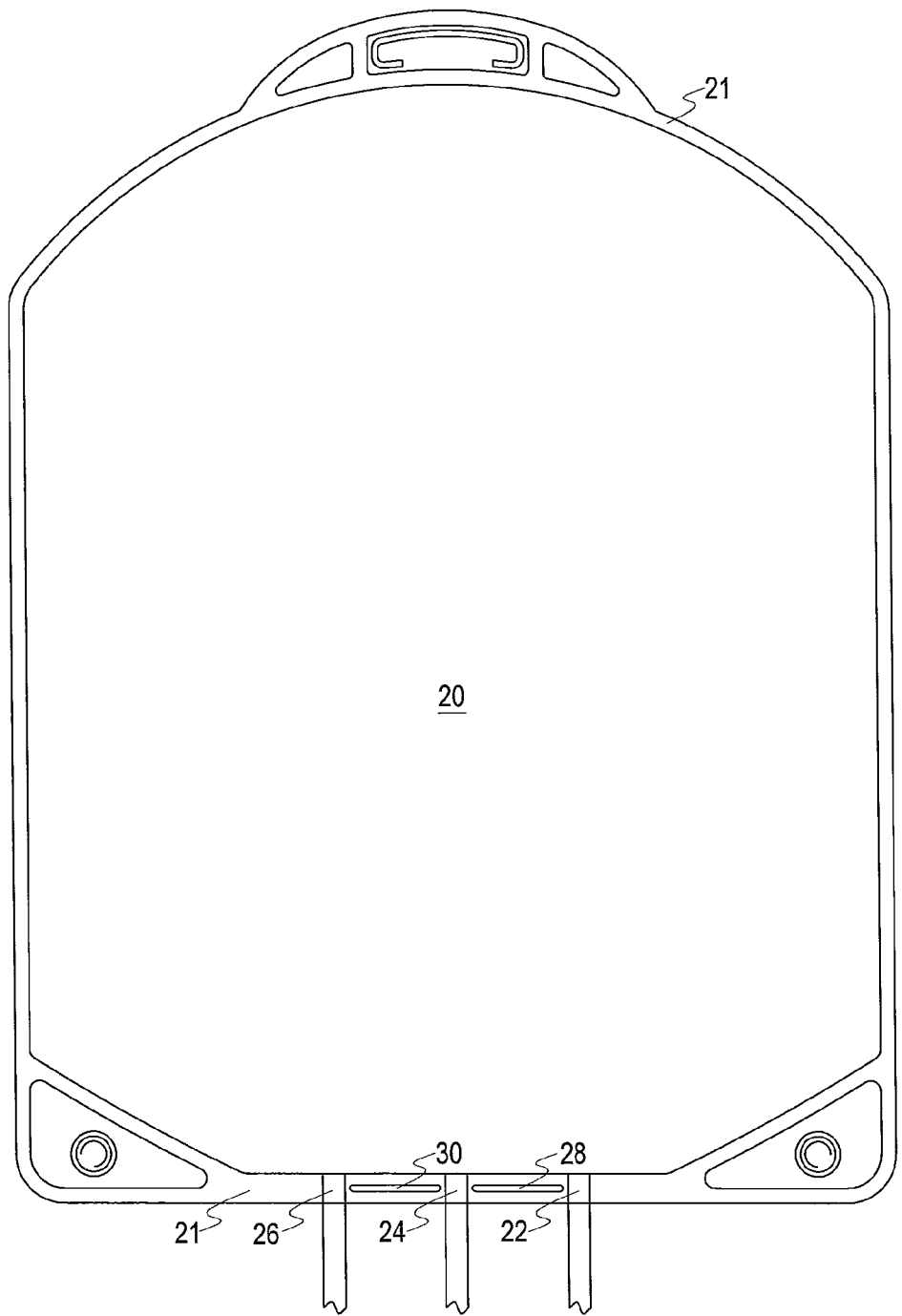
FIG. 4 depicts a fluid container, such as a blood bag, in accordance with embodiments of the present disclosure.

Turning to FIG. 4, a view of a representative container 20 or bag 20 for use with the slidable clamp 1 of the present disclosure is shown according to an embodiment. A suitable container 20 or bag 20 is typically made of a flexible, biocompatible, polymeric material and, if used as an illumination container, is photopermeable. Photopermeable means that the material is adequately transparent to desired wavelengths of electromagnetic radiation for activating a photosensitizer. In embodiments, such container also has a proper depth to allow the photoradiation to reach microorganisms at all distances from the illumination source. If the container is used to contain blood, it also is desirable for the container, such as bag 20, to have good blood compatibility. The polymeric material is typically sealed or welded around its outer border zones during manufacture to form a contiguous seal or weld 21 around all sides of the container to create a main body portion. At least one port 22, 24, or 26 or opening extending into the main body portion of the container 20 allows fluid ingress and/or egress into and out of the bag 20.

As shown in FIG. 4, there are three ports 22, 24, or 26, or openings in bag 20, in accordance with embodiments. In an embodiment, inlet port 24 allows the fluid to be decontaminated and the photosensitizer (if used) to flow into bag 20. Outlet ports 22 and 26 allow the pathogen inactivated fluid to flow out of container 20. In embodiments, a sample bulb (not shown) may be fluidly connected to port 22 and/or 26.

According to embodiments, there are at least two openings or slits 28 and 30 in the seal 21 of bag 20. The slits are located immediately adjacent to at least two of the ports 22 and 26 to be isolated, according to embodiments. In embodiments, there may be as many slits as ports, or, in other embodiments, there may be only one slit and multiple ports, without departing from the spirit and scope of the present disclosure. In other embodiments, recesses or indentations in the seal 21 of the bag 20 are used as coupling structures, instead of actual openings or slits in the seal, without departing from the spirit and scope of the present disclosure. In embodiments, the clamp is coupled to the fluid container adjacent to the port to be isolated, in which such coupling occurs without the use of slits, for example. In yet other embodiments, clamp 1 functions without recesses or indentations in seal 21 and uses other types of coupling structure(s), for example. Many types of coupling structures and/or coupling mechanisms may be used in accordance with embodiments herein.

Figure 5:
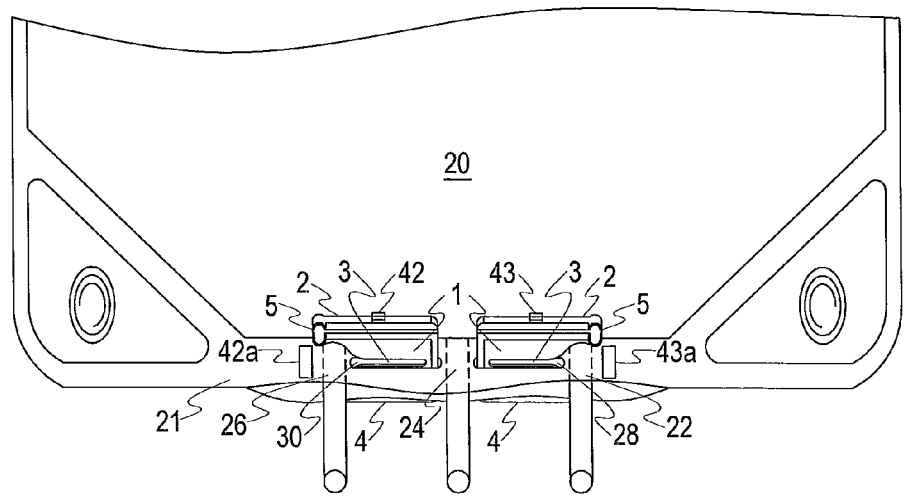
FIG. 5 illustrates a perspective view of a portion of the fluid container shown in FIG. 4, in which such portion depicts the outlet ports of the fluid container in open positions, in accordance with embodiments of the present disclosure.

While FIG. 4 illustrates the location of the openings or slits 28 and 30 in the seal 21 of bag 20, FIGS. 5 and 6 depict the open and closed positions of the slidable clamps 1 in such openings or slits, in accordance with embodiments of the present disclosure. For example, FIG. 5 shows clamp 1 in the slits 28 and 30 of the bag 20. In the open position, the distal portion 5 of the clamp 1 where the slot 3 has an increased diameter, i.e., first portion 3a, rests over the ports 22 and 26. In embodiments, the slits 28 and 30 keep the clamp 1 in the open position during sterilization and shipping, for example. In other embodiments, clamp 1 is held in the open position during sterilization and shipping, for example, by kit organizer, or spacer, 50.

As shown in FIG. 6, to seal off the ports 22 and 26, the clamps 1 slide along the slits 28 and 30 so that the slots at the narrowest most proximal portion of the clamps 1 close the ports 22 and 26. In embodiments, slot 3 thus communicates with opening or slit 28 or 30 such that slot 3 traverses slit 28 or 30 along slot 3. Outlet or exit port 22 or 26 enters slot 3 at the distal end of the first portion 3a of slot 3 and is compressed as slot 3 of clamp 1 is slid over, or moves over, outlet port 22 or 26, and outlet port 22 or 26 moves into the proximal end of the second portion 3b of slot 3. The ports 22 and 26 are now effectively closed, and fluid may be added to the bag, such as through inlet port 24, with no chance of the liquid entering the outlet ports and associated tubing. If pathogen reduction of the fluid is desired, the clamps 1 of the present disclosure effectively close off the outlet ports 22 and 26, preventing any contaminants from remaining in the ports (through trapped fluid) and, consequently, preventing the infection of the inactivated fluid in the bag 20 once the ports are re-opened. In an embodiment, the alignment indicator(s), such as 42 and/or 43, for example, on clamp 1 line up, or align, with a corresponding alignment indicator(s), such as 42a or 43a, for example, on the bag to let the user know when the clamp is in a closed position, and the port is fluidly closed.

Figure 11:
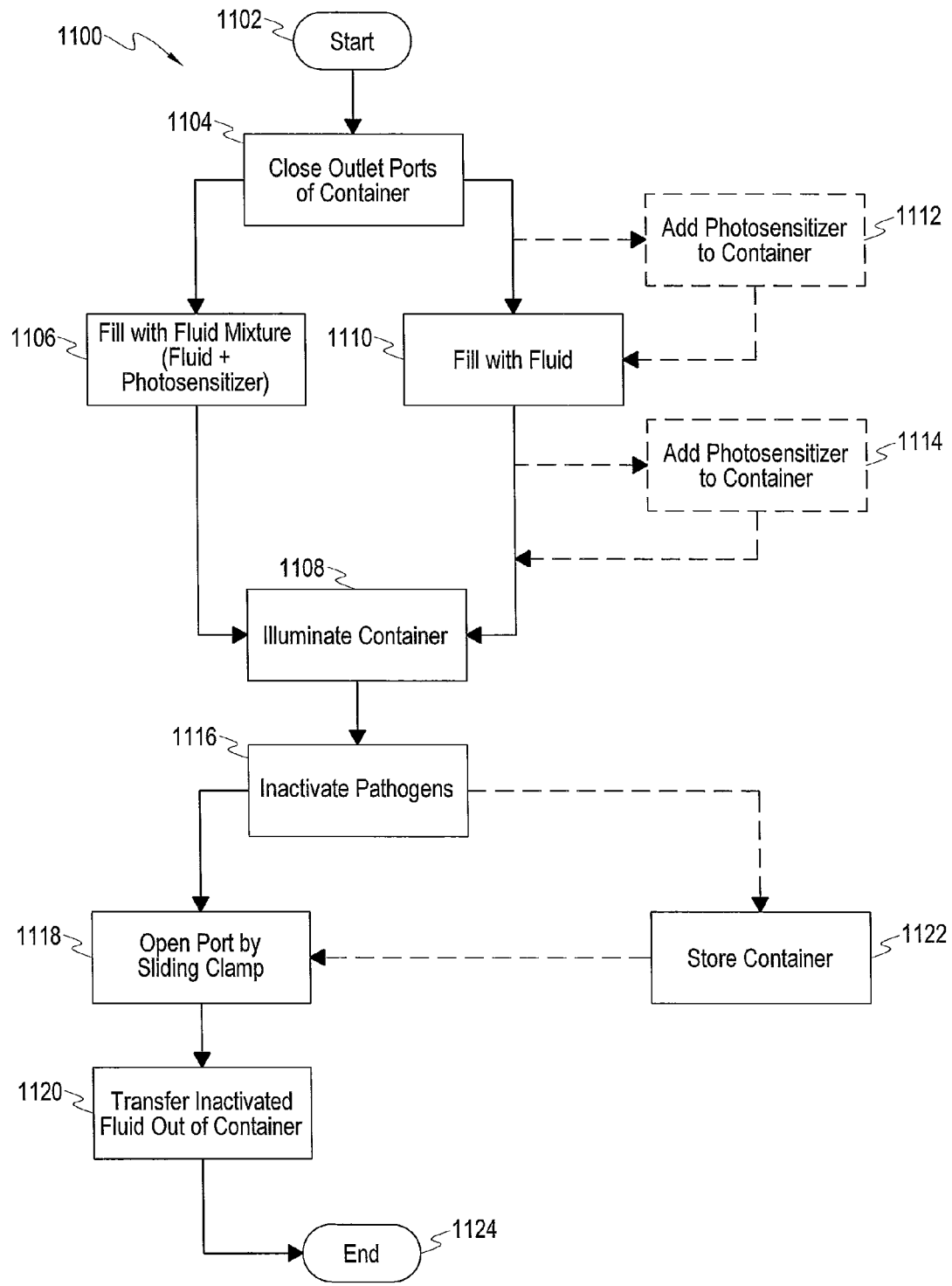
FIG. 11 illustrates a flow diagram depicting the operational characteristics of a process for inactivating pathogens in a fluid using one or more slidable clamps in accordance with embodiments of the present disclosure.

Next, FIG. 11 illustrates example operational steps 1100 for inactivating pathogens in a fluid using one or more slidable clamps to close ports, such as outlet ports, for example, of a fluid container in accordance with embodiments of the present disclosure. While outlet ports are described with respect to process 1100, FIG. 11 and the operational steps associated therewith also apply to any type of port. Start operation 1102 is initiated, and, prior to the entry of fluid into a fluid container, such as fluid container 20, for example, process 1100 proceeds to the closing, or sealing off, 1104 of the fluid outlet ports (such as outlet ports 22 and 26, for example) from the interior of container 20 through the use of slidable clamps (such as clamp 1, for example). In an embodiment, closing, or sealing off, 1104 the fluid outlet ports comprises coupling the clamp to the fluid container, in which such coupling occurs adjacent to the outlet port. The clamp is then slid to position the first outlet port in a slot of the clamp, in which the slot comprises a first portion at a distal end of the slot and a second portion at a proximal end of the slot, the first portion of the slot comprising a first width and the second portion of the slot comprising a second width. In an embodiment, the first width is larger than the second width. The clamp is then moved, from the first portion of the slot to the second portion of the slot, over the first outlet port to close the first outlet port. In embodiments, the outlet port is closed when the outlet port is positioned in the proximal end of the second portion 3b of the slot 3, for example, such that the lumen of the port is compressed entirely to create a fluid-tight seal.

Following the closing of the outlet port(s), process 1100 branches either to operation 1106 or 1110. Where process 1100 branches to operation 1106, the fluid container is filled with a fluid mixture comprising the photosensitizer and the fluid to be pathogen inactivated/reduced. In such an embodiment, the fluid mixture is flowed through an inlet port, such as inlet port 24, for example, and associated tubing into bag 20, in which the fluid is mixed with a photosensitizer before being transferred into container 20. Process 1100 then proceeds to operation 1108, in which the fluid container is illuminated for pathogen inactivation 1116. At operations 1108 and 1116, the fluid and photosensitizer are illuminated for a sufficient time to reduce or inactivate any pathogens which may be present in the fluid, without destroying the biological activity of the fluid. In an embodiment, a light source for such illumination includes a fluorescent or luminescent source providing wavelengths in the ultraviolet to visible range. While operations 1108 and 1116 are shown as separate steps according to the embodiments depicted in FIG. 11, these steps may occur in one step or additional steps, according to other embodiments.

Returning to operation 1104, in another embodiment, process 1100 branches to operation 1110 and optional step 1112, in which the photosensitizer is optionally added to the fluid container 20 before the fluid to be pathogen reduced is added. In yet another embodiment, the container 20 is first filled with the fluid to be pathogen reduced 1110, and the photosensitizer is then optionally added 1114 to bag 20 through an inlet port, such as inlet port 24, for example, and associated tubing after the fluid to be pathogen inactivated has been added to the bag 20. Process 1100 then proceeds to operation 1108, in which the fluid container is illuminated for pathogen inactivation 1116. At operations 1108 and 1116, the fluid and photosensitizer are illuminated for a sufficient time to reduce or inactivate any pathogens which may be in the fluid to produce an inactivated fluid, while not destroying the biological activity of the fluid. While operations 1108 and 1116 are shown as separate steps according to the embodiments depicted in FIG. 11, these steps may occur in one step or additional steps, according to other embodiments.

After the pathogen inactivation procedure 1116 is completed, the inactivated fluid may optionally remain in container 20 for storage 1122 until use, or the inactivated fluid may be transferred 1120 out of container 20 via opening outlet ports 1118, such as outlet ports 22 or 26, for example, and associated tubing. To transfer 1120 the inactivated fluid out of container 20, clamp 1 is slid along a coupling mechanism(s) or coupling structure(s), such as slits 28 and 30, for example, so that the distal portion, such as distal portion 5, for example, of the clamp 1 where the slot has an increased diameter or width rests over outlet ports 22 and 26, opening the port(s) 1118 to allow fluid to flow through the port(s) and transfer 1120 out of the container 20. In an embodiment, clamp 1 is removed from container 20 when or after the port is opened 1118. In another embodiment, clamp 1 remains attached to container 20 when or after the port is opened 1118. Process 1100 then terminates at END operation 1124.

With respect to the process 1100 illustrated in FIG. 11, the operational steps depicted are offered for purposes of illustration and may be rearranged, combined into other steps, used in parallel with other steps, etc., according to embodiments of the present disclosure. Further, fewer or additional steps may be used in embodiments without departing from the spirit and scope of the present disclosure.

The present disclosure's separating or isolating the ports at the point of entry into the bag or container prevents fluid from becoming trapped within the ports and corresponding tubing, creating stagnant pockets of fluid. The presence of stagnant pockets of fluid trapped within the ports and tubing may prevent photosensitizing agent from coming into inactivating interaction with any pathogens contained within the stagnant fluid pockets. Also, the opaque ports may prevent light from penetrating through the ports, preventing inactivation of any pathogens in the fluid and increasing the risk of reinfecting the previously inactivated fluid. The present disclosure also obviates the use of frangible connectors, and the problems associated therewith, to close off the ports in a container.

The present disclosure has been described with reference to an illumination bag for use in a pathogen reduction procedure. However, it should be noted that the slidable clamp(s) and slot(s) may be used with any bag or container requiring selective communication between the interior and exterior of such bag or container.

It will be apparent to those skilled in the art that various modifications and variations can be made to the apparatus, structure, and methods described herein. Thus, it should be understood that the embodiments are not limited to the subject matter discussed in the Specification. Rather, the present disclosure is intended to cover modifications, variations, and/or equivalents. The acts, features, structures, and/or media are disclosed as illustrative embodiments for implementation of the claims.

The invention claimed is:

1. A method for using a clamp to isolate a port of a fluid container, the method comprising:
    closing, with the clamp, a first outlet port of the fluid container, wherein the clamp comprises a first alignment indicator, wherein the closing comprises:
        coupling the clamp to the fluid container, wherein the coupling occurs adjacent to the first outlet port;
        sliding the clamp to position the first outlet port in a slot of the clamp, wherein the slot comprises a first portion at a distal end of the slot and a second portion at a proximal end of the slot, the first portion of the slot comprising a first width and the second portion of the slot comprising a second width, and wherein the first width is larger than the second width; and
        moving the clamp, from the first portion of the slot to the second portion of the slot, over the first outlet port to close the first outlet port;
    after the closing, with the clamp, the first outlet port of the fluid container, adding a fluid to the fluid container, wherein the fluid comprises a liquid product to be pathogen inactivated;
    adding a photosensitizer to the fluid container;
    illuminating the fluid container; and
    inactivating a pathogen in the fluid container to produce an inactivated fluid.

2. The method of claim 1, further comprising:
    after the inactivating the pathogen in the fluid container to produce the inactivated fluid, opening, with the clamp, the first outlet port; and
    transferring the inactivated fluid out of the fluid container.

3. The method of claim 1, wherein the closing, with the clamp, the first outlet port of the fluid container comprises isolating the first outlet port of the fluid container to prevent the liquid product from entering the first outlet port.

4. The method of claim 3, wherein the first outlet port is closed when it occupies a proximal end of the second portion of the slot.

5. The method of claim 1, wherein the moving of the clamp further comprises:
the slot moving over the first outlet port at the distal end of the slot; and
the slot compressing the first outlet port, wherein the compressing comprises the slot moving over the first outlet port at the proximal end of the slot such that the first outlet port occupies a proximal end of the second portion of the slot.

6. The method of claim 1, wherein the first alignment indicator is on an upper portion of the clamp, and wherein the first alignment indicator on the upper portion of the clamp aligns with a second alignment indicator on the fluid container to indicate that the clamp is in a closed position.

7. The method of claim 1, wherein the first alignment indicator is on a lower portion of the clamp, and wherein the first alignment indicator on the lower portion of the clamp aligns with a second alignment indicator on the fluid container to indicate that the clamp is in a closed position.

8. The method of claim 1, further comprising:
removing a kit organizer from the fluid container after the closing, with the clamp, the first outlet port of the fluid container.

9. The method of claim 8, wherein the kit organizer causes the first outlet port to be open during sterilization of the fluid container.

10. The method of claim 1, wherein the coupling the clamp to the fluid container comprises positioning the clamp in a first slit in the fluid container.

11. The method of claim 10, wherein a kit organizer comprises a second slit corresponding to the first slit in the fluid container.

12. The method of claim 1, wherein the coupling the clamp to the fluid container comprises positioning the clamp in a recess in the fluid container.

13. The method of claim 1, wherein the coupling the clamp to the fluid container comprises positioning the clamp in an indentation in the fluid container.

14. A port isolation apparatus, the apparatus comprising:
a fluid container, wherein the fluid container comprises a first coupling structure in a weld area of the fluid container, the fluid container comprising:
a first outlet port, wherein the first outlet port is adjacent to the first coupling structure in the weld area of the fluid container; and
a clamp connected to the first coupling structure of the fluid container, wherein the clamp comprises a slot, the slot comprising a first portion at a distal end of the slot and a second portion at a proximal end of the slot, the first portion of the slot comprising a first width and the second portion of the slot comprising a second width, wherein the first width is larger than the second width, and wherein the first outlet port is positioned in the slot of the clamp as the clamp is slid over the first outlet port to close a lumen of the first outlet port, wherein the clamp further comprises a first alignment indicator.

15. The port isolation apparatus of claim 14, wherein the first alignment indicator is on an upper portion of the clamp, and wherein the first alignment indicator on the upper portion of the clamp aligns with a second alignment indicator on the fluid container to indicate that the clamp is in a closed position.

16. The port isolation apparatus of claim 14, wherein the first outlet port of the fluid container is closed when the first outlet port occupies the second portion of the slot.

17. The port isolation apparatus of claim 14, wherein the fluid container further comprises:
a second outlet port, wherein the second outlet port is adjacent to a second coupling structure in the weld area of the fluid container.

18. The port isolation apparatus of claim 14, wherein:
the slot communicates with the first coupling structure such that the slot traverses the first coupling structure along the slot; and
the first outlet port enters the slot at the distal end of the slot, wherein the first outlet port is compressed as the first outlet port moves to the proximal end of the slot.

19. The port isolation apparatus of claim 14, wherein the first coupling structure in the weld area of the fluid container is a slit.

20. The port isolation apparatus of claim 14, wherein the first coupling structure in the weld area of the fluid container is a recess.

21. The port isolation apparatus of claim 14, wherein the first coupling structure in the weld area of the fluid container is an indentation.

22. A clamp to isolate a port of a fluid container, the clamp comprising:
an upper portion comprising an upper portion front surface substantially similar to an upper portion back surface;
a back portion connected at substantially ninety degrees to the upper portion;
a lower portion connected at substantially ninety degrees to the back portion, wherein the lower portion and the upper portion are substantially parallel to each other, and wherein the lower portion comprises a lower portion front surface substantially similar to a lower portion back surface;
a slot separating the upper portion and the lower portion, wherein the slot comprises a first portion at a distal end of the slot and a second portion at a proximal end of the slot, the first portion of the slot comprising a first width and the second portion of the slot comprising a second width, and wherein the first width is larger than the second width;
a first groove extending longitudinally along the lower portion front surface and the lower portion back surface to a distal end of the clamp; and
a first alignment indicator located on the clamp.

23. The clamp of claim 22, further comprising:
a second alignment indicator located on a lower surface of the lower portion of the clamp, and wherein the first alignment indicator is located on an upper surface of the upper portion of the clamp.

24. The clamp of claim 23, wherein the first alignment indicator on the upper portion of the clamp is configured to align with a third alignment indicator on the fluid container to indicate that the clamp is in a closed position.

25. The clamp of claim 22, wherein the second width of the second portion of the slot is substantially uniform from a distal end of the second portion of the slot to a proximal end of the second portion of the slot.

26. The clamp of claim 22, further comprising:
a second groove extending longitudinally along the upper portion front surface and the upper portion back surface to the distal end of the clamp.

27. The clamp of claim 26, wherein the first groove and the second groove are configured to align the clamp with a kit organizer.

* * * * *